United States Patent
Irons

(10) Patent No.: US 6,729,729 B1
(45) Date of Patent: May 4, 2004

(54) METHOD OF TESTING AND CORRESPONDING VISION AID

(75) Inventor: Peter Irons, Peterborough (GB)

(73) Assignee: Tintavision Limited, Peterborough (GB)

(*) Notice: Subject to any disclaimer, the term of this patent is extended or adjusted under 35 U.S.C. 154(b) by 150 days.

(21) Appl. No.: 10/030,444

(22) PCT Filed: Jul. 17, 2000

(86) PCT No.: PCT/GB00/02660
§ 371 (c)(1),
(2), (4) Date: Jan. 8, 2002

(87) PCT Pub. No.: WO01/05300
PCT Pub. Date: Jan. 25, 2001

(30) Foreign Application Priority Data

Jul. 15, 1999 (GB) .............................................. 9916635
Mar. 17, 2000 (GB) .............................................. 0006426

(51) Int. Cl.[7] ................................................. A61B 3/02
(52) U.S. Cl. ..................................................... 351/242
(58) Field of Search ................................. 351/200, 205, 351/209, 213, 216, 219, 221, 222, 233, 239, 242, 246

(56) References Cited

U.S. PATENT DOCUMENTS 4,961,640 A * 10/1990 Irlen .......................... 351/246
5,589,898 A    12/1996 Atkinson
5,883,694 A     3/1999 Mumford
6,045,515 A  *  4/2000 Lawton ...................... 351/239

FOREIGN PATENT DOCUMENTS

| DE | 19804703 | 10/1999 |
| FR | 2593381 | 7/1987 |
| GB | 2266786 | 11/1993 |
| WO | WO9844848 | 10/1998 |

* cited by examiner

Primary Examiner—Dennis W. Ruhl
Assistant Examiner—John R. Sanders
(74) Attorney, Agent, or Firm—Richard M. Goldberg

(57) ABSTRACT

A method of testing applicable to a vision aid, such as a tinted transparent overlay for placement over textual matter to be read, or selection of a tint for a vdu screen, to assist in amelioration of symptoms in dyslexia and other optical and related disorders, uses a quantitative approach to the identification of the colorimetric parameter within the three dimensions of color space applicable to the vision aid for optimal patient visual performance, and provides a test procedure in which a numerical value (the benefit value) is associated with a given value of each of the three calorimetric parameters, and a short series of similar tests on differing colorimetric parameters enables the optimum value to be interpreted whereby the optimal value may not be a value actually tested, with tasks strictly separated into array tasks and non-array tasks.

13 Claims, 6 Drawing Sheets

METHOD OF TESTING AND CORRESPONDING VISION AID

CROSS REFERENCE TO RELATED APPLICATIONS

This application is the National Stage under 35 U.S.C. 371 of International Application No. PCT/GB 00/02660, filed Jul. 17, 2000.

BACKGROUND OF THE INVENTION

This invention relates to methods of testing and/or methods of selection and/or methods of manufacture applicable to the provision of vision aids for use in optical recognition tasks including reading. A particular aspect of the invention relates to the provision of vision aids to assist in reducing the effects of dyslexia and related and other optical disorders. It is to be understood that the term vision aids includes the use of a vision aid in which the aid is provided by the use of particular calorimetric parameters in the colour of the background of a visual display unit screen.

The invention provides a new approach to the selection and/or manufacture of tinted transparent vision aids for such use.

There is disclosed in U.S. Pat. No. 4,961,640 (Irlen) a system intended for the provision of tinted spectacles which are to be worn by the user at all times during which the intended benefits are required—see column 12 at lines 21 to 23. In the system of the U.S. 640 specification the tinted spectacle elements are selected (albeit with reference to graphic data relating to the optical parameters of the spectacle elements) on the basis of data obtained by purely intuitive methods based upon the patients'own interpretation of criteria selected (see the case studies commencing at column 7 and line 30). Case 1 refers to Ann, a woman of age 21 having very detailed listed perceptual impairments. It is stated at column 8, line 1 that Ann was then diagnosed with the IVPS test attached in "Appendix 1", on which she scored 62% affirmative responses. The U.S. 640 specification does not include an "Appendix 1" so there is no disclosure relating to this test. However, it appears from the text in column 8 that this test is purely a diagnostic test related to the diagnosis of the perceptual impairments mentioned above. It is stated that clear glass lenses having no vision correction other than their tint and optical density, taken from the lens set specified in "table 1 above" were superimposed in a lens frame . . . The pages of the U.S. 640 specification likewise do not include a "table" so it is difficult to know what this disclosure means. However, what is clear is what is stated (at column 8 at line 8) that "in the case of Anne it appeared that the symptoms stated above were minimised by superimposition for both eyes of lenses pink 2 and green 1". It is then stated that Anne was given a conventional opthalmological examination and that (column 8, line 18) when fitted with the pink and green tinted lenses the patient reported a dramatic improvement in depth perception with clear peripheral vision. Other improvements are also noted including increased reading rate and the elimination of eye strain.

It needs to be clearly understood that the disclosure in the U.S. 640 specification in relation to Case 1 (Anne), case 2 (Betty), and Case 3 (Clio) entirely adopts the same intuitive approach to the identification of the calorimetric parameter applicable to the tinted spectacles to be used for improving vision. Thus, it is stated (column 8 at line 8) that "in the case of Ann it appeared that the symptoms described above were minimised by superimposition for both eyes of lenses pink 2 and green 1". In other words, the tester just guessed which were the right lenses, tried them, and asked the patient how she perceived the result. The same applies to Betty and Clio. Likewise, there is no recognition in the U.S. 640 specification of the importance (or even the existence) of "colour space". By colour space we mean (in one aspect of the invention in which the concept may be identified as "perceived colour space") the three-dimensional concept of the three calorimetric parameters which any tinted transparent vision aid possesses, namely values with respect to hue (or frequency) and saturation (or density) and luminosity (or total light energy).

In relation to hue (or frequency) the calorimetric parameters may alternatively be identified as. "biological/physical colour space" based on values on red/green/blue scales which thus provide an alternative definition of colour space. This latter approach (red/green/blue or R/G/B values are of particular relevance in relation to the testing and use of the method of the invention in relation to VDU screens.

Additionally, the U.S. 640 specification does not recognise the significance of types of optical tasks to be undertaken by the patient being tested.

While it is not disputed that the techniques disclosed in the Irlen specification can produce worthwhile benefits in terms of enhanced interpretation of visual data, we have discovered that the benefits available from the use of tinted screen devices (whether used as overlays placed on printed text, or used in relation to VDU screens as background colour or as a front-mounted screen tint element, or even in spectacle elements) are enhanced to an extent which is generally thought somewhat unlikely when the calorimetric parameters relating to the tinted elements are determined on a quantitative basis and applied to the selection or production of the optimum tinted element for a given patient. Indeed, our data suggest that far from the perhaps expected situation of diminishing returns for increasing accuracy in screen tint selection, in fact the opposite is true and the returns for such accuracy are far from diminishing and actually disproportionate to the numerical value of the three values in colour space (as discussed elsewhere as between an ill-matched screen tint and a well-matched one.

We have also discovered that not only are quantitative tests beneficial to an unexpected extent, but also that it is most important to separate the types of optical tasks to be undertaken by the patient into array tasks (such as reading or recognising rows of data, and non-array tasks such as the searching for and eventual finding of one or more hidden items on a page of data. We have thus discovered that the difference between array and non-array includes substantial differences in the use of the muscles of the eye which leads to fundamental differences in the optical problems associated with these two types of tasks. If the two types of tasks are confused or mixed as in the prior art such as the U.S. 640 specification, the results of the tests are, we have discovered, relatively low in value.

Finally, we have also discovered that in the methods of testing applicable to the provision of tinted transparent vision aids, the provision of an optimum such aid for a given patient requires attention to the three-dimensional aspects of the calorimetric parameters, namely the three-dimensionally plotable values of hue or frequency and saturation or density and luminosity or total light energy. Unless these three values of perceived colour space (or the red/green/blue or R/G/B values of biological/physical colour space, see discussion above) are taken in to account, the calorimetric parameters of the vision aid resulting from a testing procedure can only be, at best, a very rough approximation to the optimum values needed by the patient. There is no recognition in the U.S. 640 specification of this requirement nor of the distinction between array and non-array tasks.

SUMMARY OF THE INVENTION

An object of the present invention is to provide methods of selecting and/or making and/or using vision aid devices providing improvements in relation to one or more of the matters discussed herein or improvements generally.

According to the inventor there is provided a method and apparatus as claimed.

In an embodiment of the invention the method for quantitative determination of the calorimetric parameters (in three-dimensional colour space) of the tinted screen device, which in the embodiment forms the visual aid device, comprises monitoring the response of the patient to systematic test procedures on a numerical basis and recording the resultant test data on a graphical basis. The graphically recorded data is then available for interpretation with respect to the optimum values of the calorimetric parameters, and the next step in the method is to make such an evaluation whereby a relatively modest number of numerical data values can permit the relatively exact determination of the optimum value of the relevant parameter for the patient in question. We have discovered that the presently-available optimum indicator for quantitative determination of the calorimetric parameters is Rate of Reading (RR) in accordance with a systematised procedure for such RR determination. Alternatively, eye movements may be monitored and quantified during standardised tasks such as reading or another array task. Likewise, the method of the invention is also applicable to non-array tasks and quantitative and/or numerical data may be obtained for example on the basis of the time taken to find a hidden element within an area of data and/or a quantitative measure of eye movements occurring per unit time while carrying out such a task.

Thus, the other indicators which are considered also suitable as the basis for the quantitative determination step of the embodiments of the present invention include indices of eye movement during certain standardised procedures such as reading (or any other array task) or (but not both) non-array tasks, whereby these eye movement data indices provide numerical measures of the patient's reaction to the use of a sequence of graduated (in three-dimensional colour space) calorimetric visual aid test elements such as tinted filters of screens, or tinted background colours in VDU screens etc.

The embodiments of the invention take as their starting point for the improvements provided by the invention the fact that the proposals of the prior art simply rely upon the intuitive interpretation of technical improvements in tinted screen amelioration of optical condition symptoms and see no basis (or perhaps no need) for determining these matters quantitatively regardless of the improvements which might thereby be available. By the discovery that the adoption of the inverse route (not involving assessment by the patient at all and basing itself on externally determinable data), the embodiments of the invention provide a new approach to the calorimetric determination of screen and other visual aid data by a hitherto unexplored route which surprisingly gives unexpectedly beneficial results. Likewise, the prior art includes no appreciation of the nature and the need for separation of array and non-array optical tasks, nor apparently any appreciation of the significance of the use of all three parameters of colour space. By separating array and non-array tasks and by testing with respect to all three-dimensions of colour space and performing these tests on a quantitative basis, the present invention embodiments provide significant improvements.

A particular aspect of the embodiments of the present invention relates to the interpretation and use of the test data obtained in, for example, the Rate of Reading test and/or the occular movements test. It is particularly significant that the embodiments of the present invention do not rely on self-assessment or an intuitive approach to the quantitative interpretation of the test results at all. Such is the province of the prior proposals and of the starting point for the tests carried out in the method of the present invention. The embodiments of the present invention obtain quantitative data by means of simple and reliable observational steps which are not open to subjective interpretational errors. Thus, whereas in the methods of the prior art, subjective assessment of the benefit obtained with a given hue or tint of test spectacle element on the part of the patient is required with, doubtless, an answer on the lines of: "yes, quite good" or "no, not very good". In contrast, the embodiments of the present invention take the numerical data obtained during the test procedure by counting rate of reading in terms of words per unit time (and such counting may be automated by a suitable programmed computer system), or else the numerical value attributable to eye movements per unit time in accordance with a standardised test protocol, and uses these values as a quantitative expression of the benefit value of the vision aid under test. What is more, the embodiments of the present invention do not rely upon just selecting the particular one of the test elements which provides a better result than the others, but by means of analysis or interpretation of the numerical or other quantitative data the embodiments enable the selection of that particular value (in relation to three-dimensional colour space), which (by use of a short series of test results,) can be seen to correspond to the optimum result. In this connection, where the results are interpreted by a graphic technique or the like, the use of template data from a data bank of previous patients'test results enables informed interpretation of the test data (with respect to all three colorimetric parameters) for a particular patient to be carried out. In other words, although the profile of the plot of (for example) reading rate against the calorimetric parameters will vary from patient to patient, there is an underlying plot general profile which can be used to assist interpretation.

In the embodiments the three calorimetric parameters of the vision aids relate either to hue and saturation and luminosity and can be recorded (for any given vision aid) by a point in perceived three-dimensional colour space, or the corresponding R/G/B values in biological/physical colour space. These variables represent the parameters for providing vision aids which enable the matching of vision aid variables to the corresponding personal variables in relation to patients suffering from visually-related disorders such as dyslexia (in relation to array tasks) and the related disorder (in relation to non-array tasks), and the symptomatic alleviation of these difficulties and related ones.

The method of the invention may be practised in various ways including the use of the method as a means for identifying the point in colour space corresponding to the optimum requirements of a given patient. It is then merely a practical question as to whether this set of three parameters is simply selected from an array of closely spaced (in terms of the three variables) "tinted screens/vision aids, or whether there is then set in motion a step to produce such a vision aid using the three parametric values and appropriate manufacturing techniques. There is available a manufacturing apparatus for such tinted screens which is capable of producing same relatively quickly on demand once the required parameter values have been identified. The present invention applies both to the mere selection of such tinted screens or filters and to their manufacture and indeed to the provision of other means for applying the identified calorimetric parameters to a patient's eyes, such as by causing a vdu screen to be appropriately coloured.

It is to be understood that a particularly important embodiment of the present invention relates to the provision of a vision aid in the form of a vdu screen adapted to provide, as the screen background to the text or other graphics displayed on the screen, a colour having a quantitatively-determined set of calorimetric parameters these having been determined by optical tests (usually in relation to the screen itself), as a result of which the user's ability to interpret data displayed against the background colour on the screen is maximised. The colorimetric parameters in relation to this aspect of the invention may comprise the basic three-dimensional perceived colour space parameters of hue, luminosity and density or may comprise the relevant red/green/blue or R/G/B values in relation to biological/physical colour space. In an embodiment described below relating to the use of the invention in relation to vdu screens, in addition to the R/G/B values being determined quantitatively, the technique also permits the related luminosity values likewise to be determined and/or optimised by means of quantitative tests.

BRIEF DESCRIPTION OF THE DRAWINGS

Embodiments of the present invention will now be described by way of example with reference to the accompany drawing in which.

DETAILED DESCRIPTION

Figure 1:
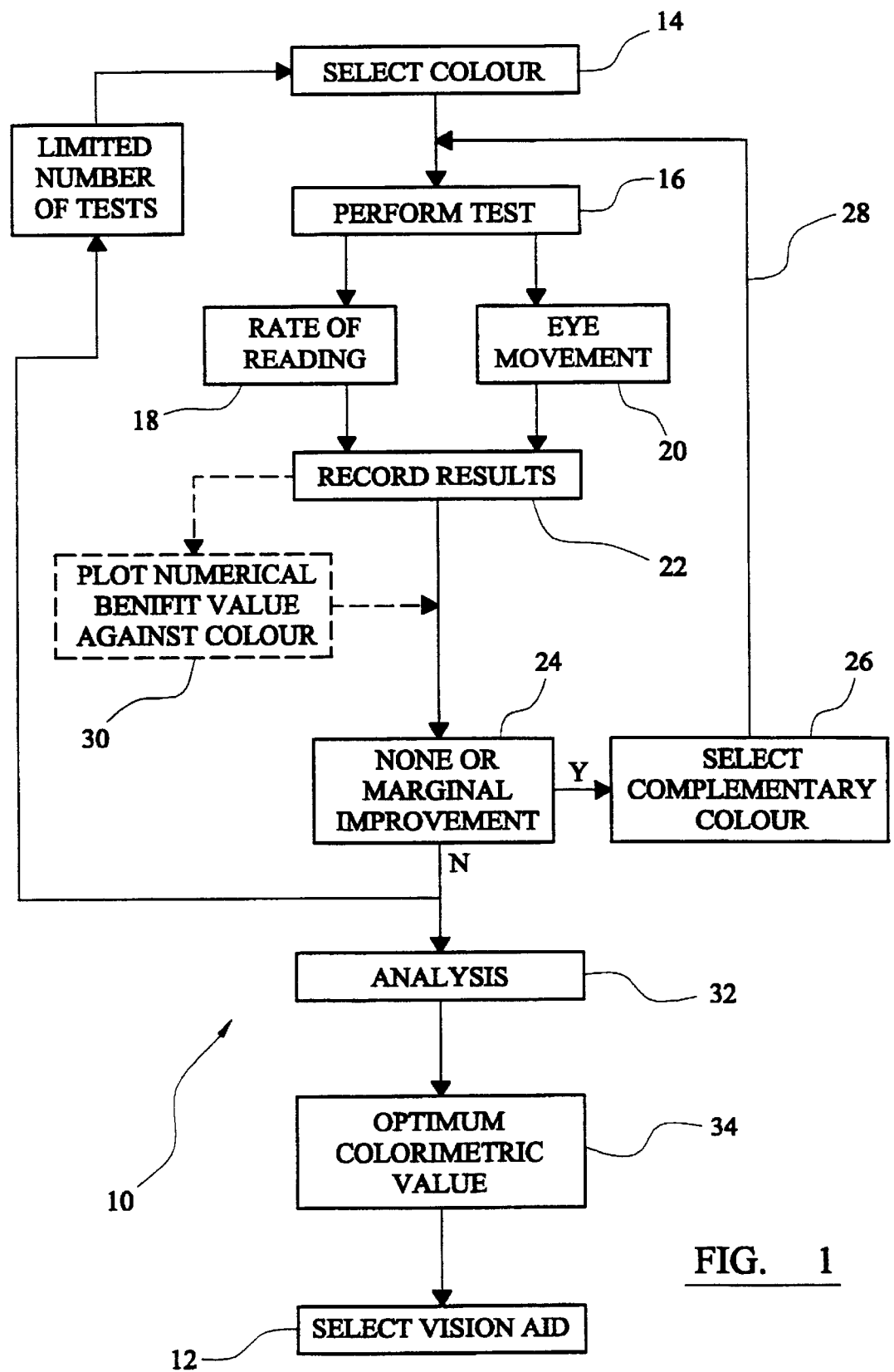
FIG. 1 shows a flow diagram representing steps in an embodiment of the present invention including an indication of certain alternative procedures.
Figure 2:
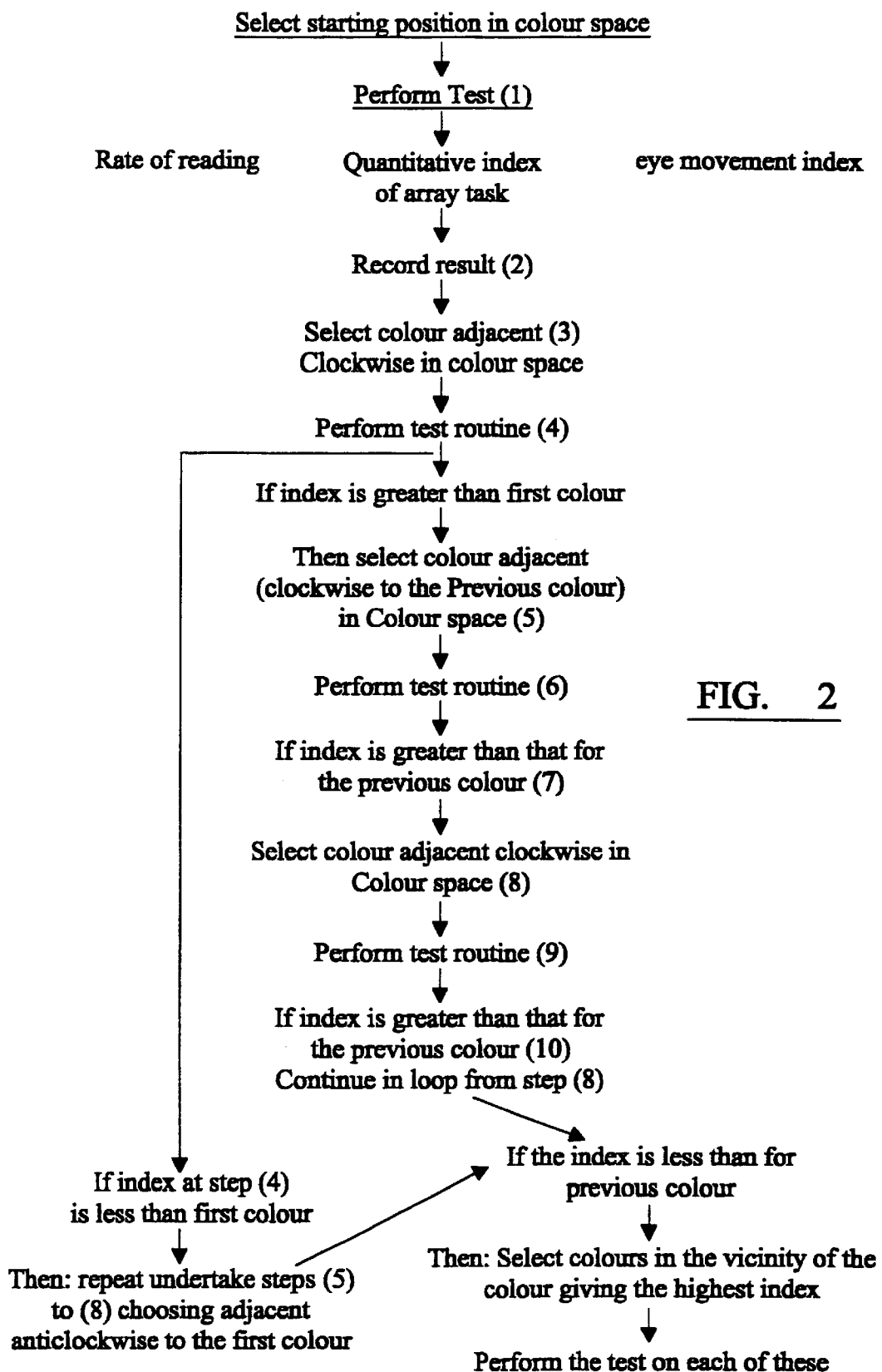
FIGS. 2 and 2A show in more detail the procedures generally identified and discussed below in relation to FIG. 1.
Figure 2A:
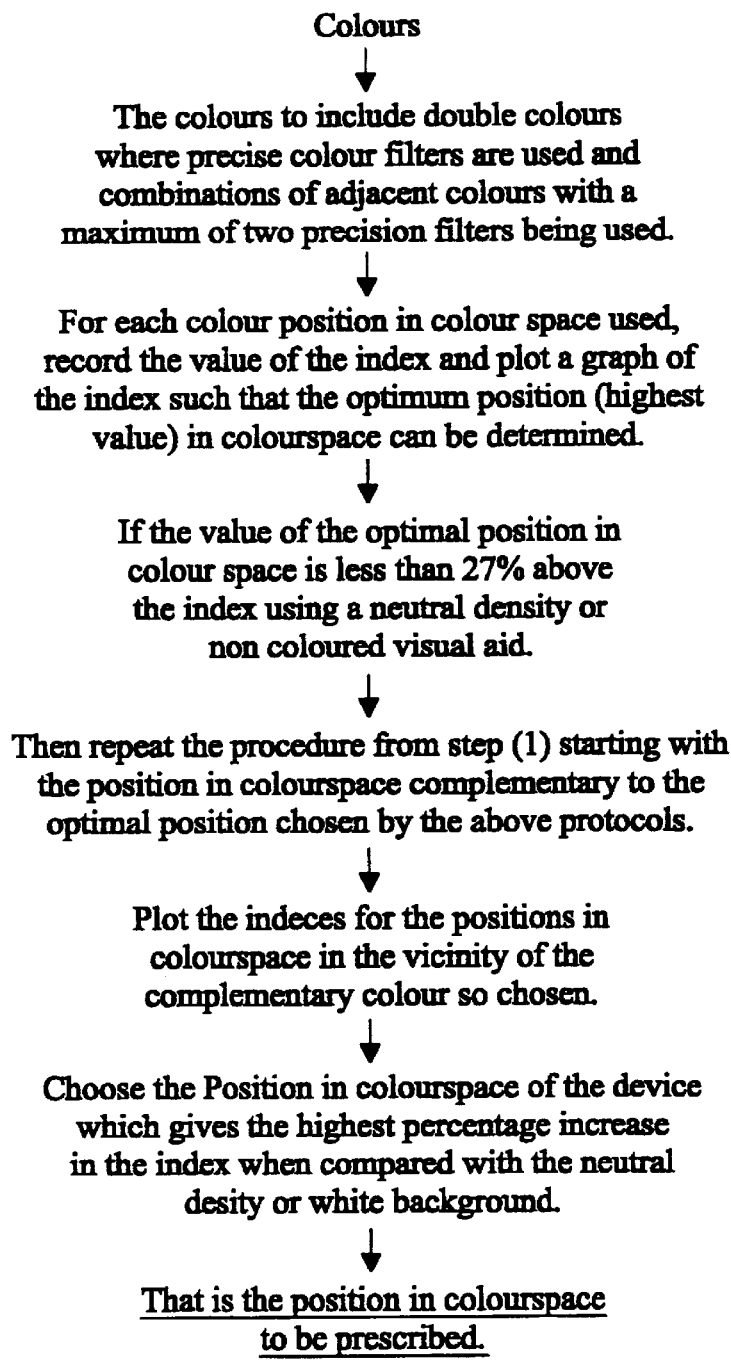

FIG. 1 shows a flow diagram representing steps in an embodiment of the present invention including indications of certain alternatives and other optional procedures.

FIG. 1 illustrates a method 10 of testing applicable to the provision of a vision aid 12 having three calorimetric parameters in colour space. The vision aid may for example be a transparent tinted plastic overlay for use in assisting the reading of array or non-array matter. Likewise, the vision aid may be provided in the format of the selection of the calorimetric parameters as the background colour or tint for a visual display screen. In such a case, the vision aid is not in a form having an actual physical presence, but consists of the provision in the screen of the identified calorimetric parameters (in colour space), whether in relation to hue and luminosity and density or in relation to R/G/B values with or without luminosity determination, which are obtainable from a vdu by means of the appropriate control/instructions to its color control system. Other vision aids included tinted spectacles and tinted screen cover devices for visual display units not having a colour control system.

It is envisaged that the invention may ultimately be substantially automated in terms of test procedures utilising dedicated software able to provide the relevant array and non-array tasks in separate optical tests and likewise able to provide by means of the vdu system's colour control system the required values of the three parameters of colour space. It may also be a simple task to provide the relevant timing or other measurement systems for obtaining quantitative data on a timing or other basis.

In accordance with the method of the invention, a first step comprises providing a vision aid 12 having a chosen value of each of the calorimetric parameters. In this first embodiment, the vision aid is in the form of a transparent plastic overlay (not shown) and in the first step of the method (shown in the drawing as "select colour" 14), a test vision aid is selected from a range of such aids as a basis for the first test to be performed by the patient. Such selection may be made on an intuitive or experience basis by the tester, or may be done in a routine procedural way, for example by commencing with the mid-range value from the relevant range of test hues or tints.

The next step in the method comprises assessing the visual benefit provided by the test vision aid, and this step is shown in the figure as "perform test" 16. In this embodiment the test employed is a standardised Reading Rate test in which the patient is required to read a section of standardised text under standard conditions and employing the vision aid 12 selected in accordance with step 14.

Further details of the Reading Rate test are set out in Example One below and attention is directed thereto.

In FIG. 1 the Rate of Reading test is indicated at 18 and an alternative test identified as Eye Movement is shown at 20. The Eye Movement test is carried out by monitoring the occular movements of the eyes during a period of standardised occular activity such as reading for an array task, or searching for a hidden data item (for a non-array task). The occular movements are monitored by a Scleral Coil Device, which is available in the United States as a locally manufactured research tool. The Scleral Coil approach uses orthogonal magnetic fields that induce a current in a Scleral Coil attached to the eye so that when the eye rotates the induced current changes. There are two types of systems namely the induced current system which directly measures that current by conductors from the Scleral Coil and the back emf system in which the induced voltage is picked up from inductor coils. The apparatus can also be adapted to allow torsion effects in the eye to be monitored likewise. From this apparatus quantitative data if so desired in numerical format, can be obtained corresponding to the dynamics of eye movements occurring and these values can then be assessed in a manner corresponding to that of the Reading Rate test results.

Thus, in accordance with the method of the invention, the step of assessing the visual benefit provided by the vision aid is carried out by means of the optical Rate of Reading or Eye Movement tests (in relation to array or non-array tasks) using the selected test vision aid 12 to identify the patient response to that vision aid under the test conditions. This response is observed in terms of Rate of Reading or in terms of Eye Movement on the above-quantitative basis, and that numerical data (or such data represented otherwise) represents the visual benefit of the selected vision aid calorimetric parameters to that particular patient.

The quantitative data obtained by the above-described last preceding test step is then recorded, 22, in relation to its position in colour space and if the value of the benefit or improvement is only marginal then a repetition step is needed on the basis of a complementary colour for the test vision aid (complementary in terms of colorimetric parameters) and the sequence of steps above-described is then repeated. In FIG. 1, this repetition route is indicated at 24 (marginal-improvement) and 26 (select complementary colour) and 28 (return to "perform test").

In the case where the numerical value of the test results does not lead to the selection of a complementary colour and a repetition of the test, the results are recorded by, for example, plotting the numerical benefit value against colour—see step 30 as described above.

The recorded test results, whether plotted numerically or otherwise, are then analysed at 32, for example by a dedicated pc having a suitable database and software programme for interpretation of a limited number of test results applicable to a given patient, so that the optimum calorimetric parameter value 34 can be selected and used for the identification of the exact vision aid 12 required by that patient for their optimal vision enhancement.

Examples two and three show test result data for embodiments of the invention in terms of reading rate (RR) for unscreened/untinted white text ("RR white") and with screen tints based on intuitive, (guessed) and optimal (by use of the method of the invention) techniques. The numerical reading rates are self-explanatory and the benefit of the optimal values for the calorimetric parameters is readily seen in most cases.

Figure 3:
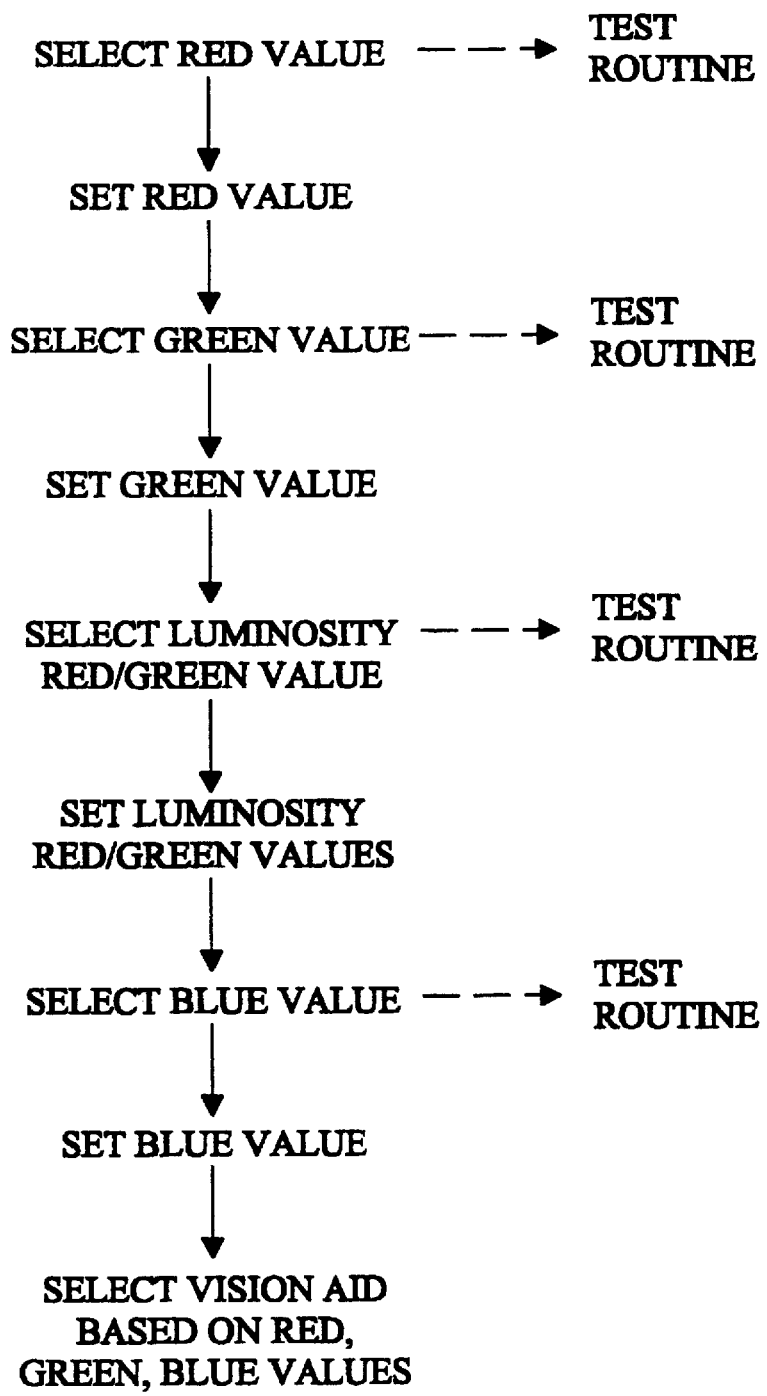
FIGS. 3 and 3A show an algorithmic procedure and a related test routine, respectively, applicable to the selection of red and green and luminosity and blue calorimetric parameters in relation to an embodiment of the invention.
Figure 3A:
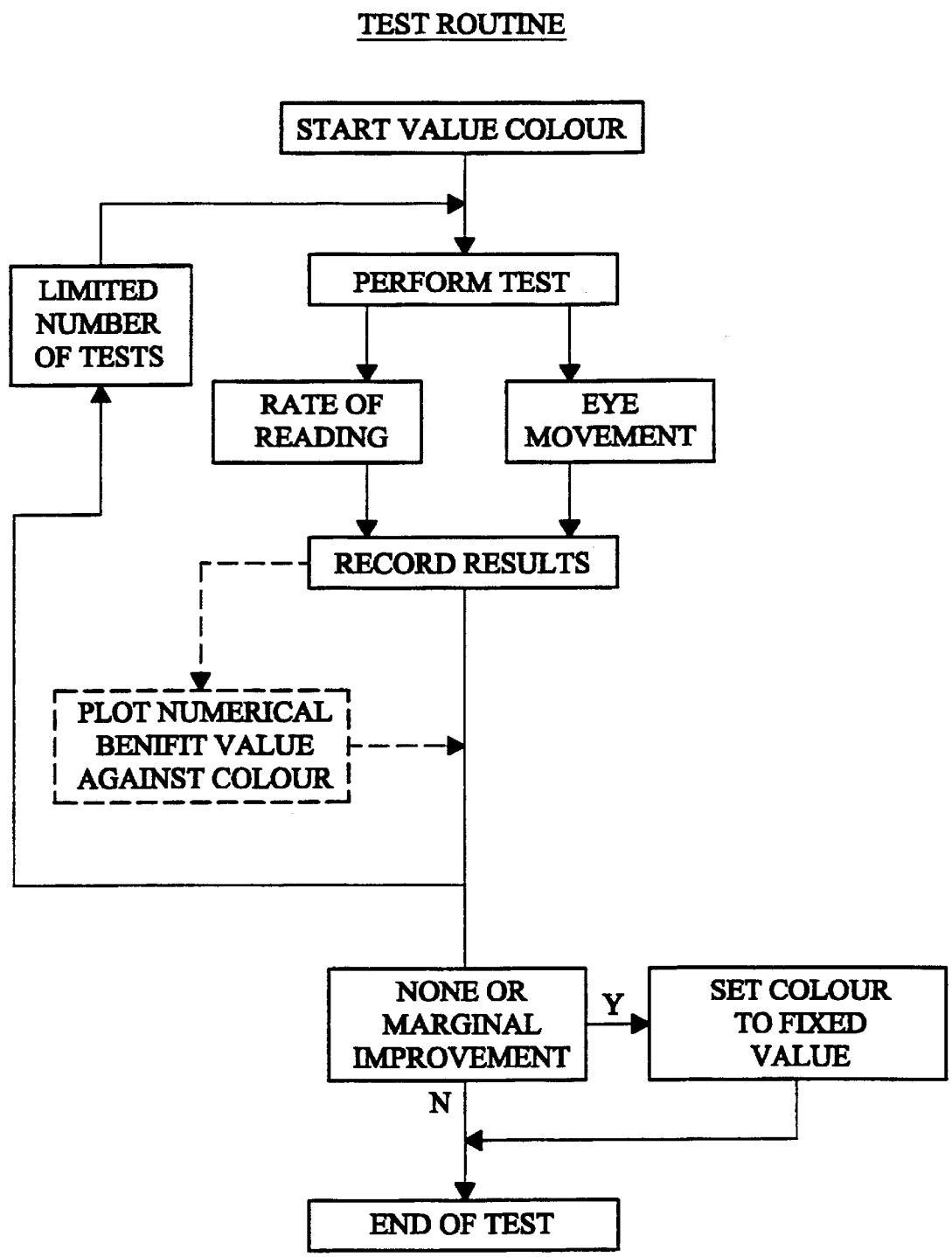
Figure 4:
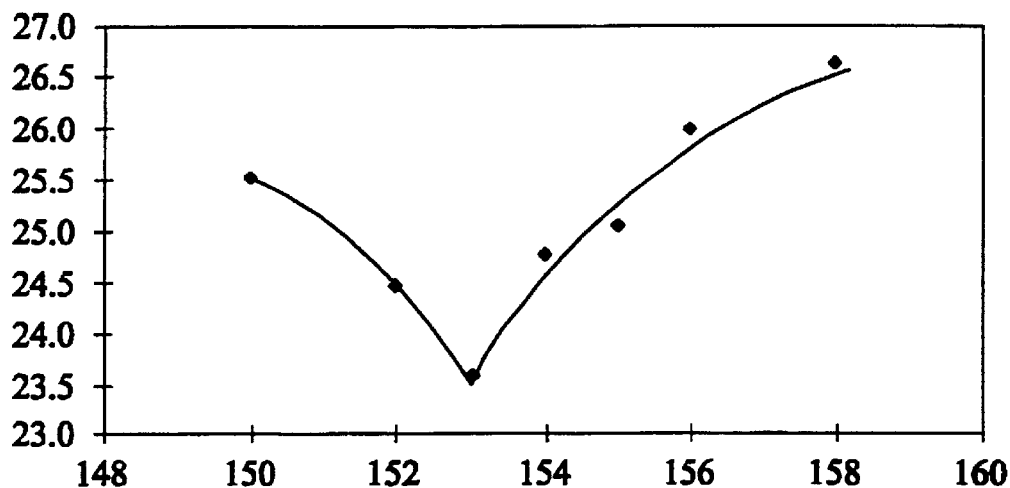
FIGS. 4 and 5 show graphic representations of the rate of reading (expressed in terms of the time taken to read a given number of words so that minimum time represents maximum rate) plotted against the relevant calorimetric parameters and showing the optimal values of the latter clearly identified.
Figure 5:
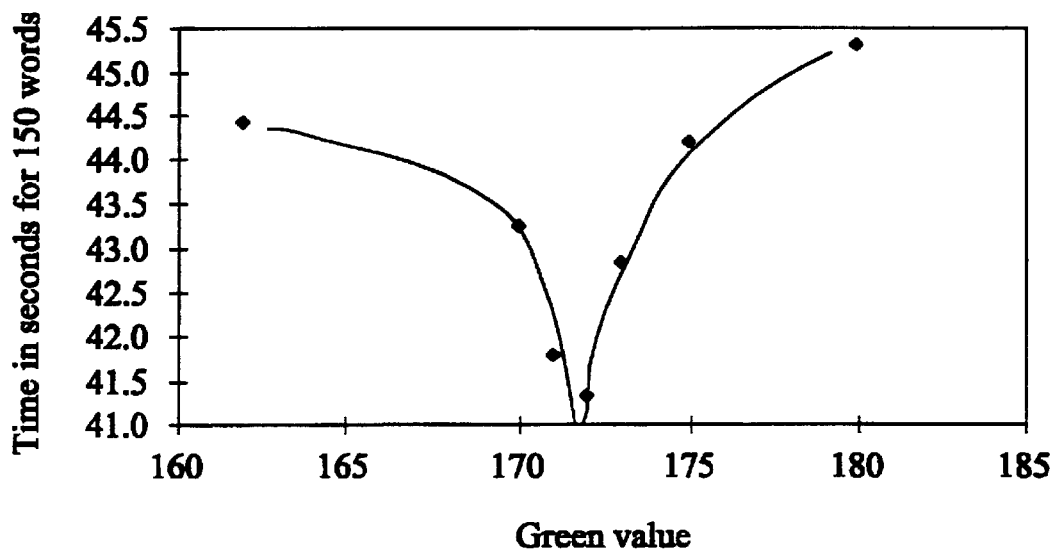

Turning now to the algorithm and test routine shown in FIGS. 3 and 3A, these identify the related sequence of testing steps carried out in relation to an embodiment of the invention employing a vdu screen employing the relevant technical provision for adjustment of red/green/blue values and luminosity, whereby optimisation of these colorimetric parameters can lead to the dramatically beneficial results to be seen in FIGS. 4 and 5 of the drawings. Thus, as shown in FIG. 3, the procedure involves the determination of the relevant red value as a first step and employing the test routine of FIG. 3A which is self-explanatory in terms of its text identifying test steps and the sequence thereof. Having determined the relevant red value which optimises reading rate (in terms of the time taken to read a given number of words for example 150 words) the corresponding tests are performed in relation to green and then in relation to luminosity and then in relation to blue and these optimised values are in each case set in relation to the colorimetric parameters control system of the vdu screen.

It is particularly noteworthy that the values of the calorimetric parameters which are being tested in the results shown in FIGS. 4 and 5, namely red and blue in relation to FIG. 4 and green in relation to FIG. 5 show very marked peaks in relation to reading rate which are interpretable as indicating a very close relationship between the effect of these calorimetric parameters and a patient's ability to interpret graphic data, which is the basis of the present invention. We have discovered that the relationship is extremely sensitive and precise and responds directly and in a determinable way to the variation of the calorimetric parameters.

The embodiments of the invention enable determination of calorimetric parameters to optimise visual performance or edge detection in terms of speed and/or stamina. The precisely determined calorimetric parameters have been found to have therapeutic effects on patients in terms of affecting beneficially edge detection, and boundary condition capabilities. This is believed to be due to a beneficial effect on the neurological system resulting from enhanced edge detection on the visual/auditory/logic areas of the brain.

In many embodiments of the invention the patient uses the R/G/B values determined by the method of the invention to pre-set their computer's vdu unit for optimal results for themselves in terms of visual interpretation of graphic and other data. The optimisation of this process has been found to produce enhanced reading/interpreting ability in relation also to white paper pages without the need for an overlay. It has also been found that repeated testing at chosen time intervals produces further beneficial results due to the fact that individual's colour requirements change with time.

EXAMPLE ONE

Protocols for the choosing of Optimum Precision Filter or combination of filters, for persons with text problems associated with colour Procedure
1. General discussion with the testee
about their experiences with text.
Encouraging them to feel free to talk
about any visual discomfort.
2. Present the Test sheet to them and
ask them to look at the sheet during your
filling in of the Data Sheet. Ask them to
see if they can find any words on the
sheet.
3. Complete the Data sheet up to
'Response to test sheet'.
4. Continue with the Record Sheet,
while the testee is still viewing the Test
sheet.
What happens when reading
A list of the experiences of the testee.
· Maximum reading time
· The pattern of reading including rest times
· Symptoms from the outset
· Symptoms if normal reading time is exceeded
e.g. blurring, movement, headaches, tiredness
Unprompted comments on viewing random letters
Record comment made by the testee, but also mark on
the record sheet the area of text which they can see
clearly when looking at the centre of the sheet.
Using the Tintavision 'Clear area' assessment
overlay assess the diameter of the clear vision area..(
record on the 'Data sheet.'
Do any of these occur
Record with a tick in the box. Make any additional
annotation that will make the comments clearer at a
later date.
Exploring Colour Space
1. Present each overlay in the correct number
sequence.
Ask the testee how the text appears under each filter,
when compared with the rest (white) of the sheet.
+....better than
0.....same as
−....worse than.
Record on the sheet for each filter in turn.
(Note..if the client has shown a positive response to the
grey sheet as well as to a wide range of coloured
filters it is advisable to re-test all of the coloured
filters in combination with the grey filter. Follow the
number sequence again. For some people there
appears to be a need to reduce the light intensity in -continued Protocols for the choosing of Optimum Precision Filter or combination of filters, for persons with text problems associated with colour addition to a change in the position in colourspace.)
2. With the selected filters (+).
Place the last two next to each other on the test sheet.
Ask the testee to decide which one gives the clearest
view of the text.
Place another + in the relevant sector of the record
sheet.
(NOTES.
a..: Check for left/right effects in the testees choosing. Especially when the
filters are near each other in colourspace. Similarly check for focusing
problems by reversing top and bottom in filter pairings. If there is an
effect
use this to modify the procedure to match the optometric problems of the
testee)
b. Where there are difficulties in deciding include the Tintavision 'clear
area assessment overlay' above the text and Precision overlay.
3. Place the next chosen filter next to the one just
chosen.
Ask for the preference.
Mark the Record sheet with another +. (If this is the
new filter, then place two + in the relevant sector.)
4. Repeat '3'
If the same filter is chosen as in '3' put another + in
the sector.
If the new filter is chosen place 3 × + in the new
sector.
5. Repeat until ALL chosen filters have been used.
(always ensure that the 'chosen filter' has more '+'
than the one rejected.)
6. On the record sheet there will be a pattern of +, 0
and − which indicate the area of colour space where
the final colour is likely to fall.
7. Using the same procedures as for 2 to 5 explore the
testees response to the combinations of double sheets
in the vicinity of the preferred filter.
   e.g.     Pink.........Pink/Pink
             Pink.........Pink/Purple
             Pink.........Pink/Rose
             Purple/Purple
             Rose/Rose
- Find the preferred filter or filter combination.
Use the declared symptoms to help the testee make the
decisions. They may all look similar to the testee.
Sometimes they will need more time than at the earlier
stages to make a choice.
Warning
If the chosen colour lies opposite a cluster of _ + and
surrounded by 0, then compare also with doubles
opposite....e.g. if the final choice was the Lime green in
the example of Record sheet included in this pack.
Record the clear area which can be viewed using the
Tintavision clear area assessment overlay.
After completion of the choice, you need to move to
the Objective assessment of the gain experienced.
Objective Analysis
1. Rate of reading (wpm)
The Wilkins Rate of Reading Test
· Version 1.......filter
· Version 2.......white
· Version 3.......white
· Version 3...white..repeat
· Version 4.......Filter
Calculate.....    Average white on version 3 (RRw)
                   Average filter (RRc)
                   % Gain with filter (RRc-RRw)/RRw
2. Complex Text
If the Rate of reading is greater than 150 wpm and the
% gain is less than 5%.
Choose a section of complex text of approximately
150 words.. Time the testee reading it silently.
First with the filter
Second on white.
Calculate the % gain.
Ask the testee to read the passage aloud.
With the filter -continued Protocols for the choosing of Optimum Precision Filter or combination of filters, for persons with text problems associated with colour No filter.
Record(Subjectively)
a. The difference in fluency
b. The comment of the testee regarding comprehension
and ease of reading.
3. Arrange for a repeat test in 6–8 weeks.
Repeat.        a. Colour choice procedure
                 b. Objective analysis protocol.
                 c. Comment on the experience of the
user.
If there is an obvious sustained gain advise on the
use of Precision Tinted spectacles.
Addendum
For Adults.
For some clients the Rate of reading test will
deliver a reduction in reading speed when using the
prescribed overlay( combination). This appears to
be associated with a change in occulomotor control
and is associated with an increased fluency and
comprehension.
It is rarely seen in clients with a RR less than 150
words per minute ( Wilkins Rate of reading test).
It is likely that this effect will be seen with
complex text as well.
It is important then to make use of the other data
such as the 'Clear area assessment' in making the
prescription decision.

EXAMPLE TWO

| RR white | RR intuitive | RR optimal |
|---|---|---|
| 127 | 178 | 178 |
| 130 | 185 | 203 |
| 138 | 140 | 168 |
| 140 | 190 | 221 |
| 176 | 217 | 217 |
| 97 | 105 | 116 |
| 131 | 174 | 206 |
| 107 | 117 | 154 |
| 57 | 104 | 145 |
| 129 | 130 | 168 |
| 168 | 189 | 225 |
| 156 | 166 | 217 |
| 118 | 149 | 167 |
| 112 | 111 | 143 |
| 128 | 149 | 162 |
| 114 | 122 | 161 |
| 159 | 182 | 199 |
| Average 128.6471 | Average 153.41176 | Average 179.4118 |

| | | |
|---|---|---|
| Average gain on intuitive colour | 24.8 | 19% |
| Average gain on Quantitatively derived colour | 50.8 | 39% |

By the use of a quantitative approach to determine the gain to the client the % gain in effectiveness of the visual system is doubled. We have evidence that this gain is accumulative at the second and subsequent consultations. This gain is not so clear cut when a non-optimised colour is prescribed.

EXAMPLE THREE

| Persons | Rate of reading (RR) on White | RR on optimal colour | % Gain Optimal | | % Gain Intuitive | | Rrintuitive |
|---|---|---|---|---|---|---|---|
| A | 114 | 119 | 138 | | 21 | | 4 |
| B | 210 | 317 | 455 | | 117 | | 51 |
| C | 57 | 57 | 57 | | 0 | | 0 |
| D | 101 | 102 | 104 | | 3 | | 1 |
| E | 73.5 | 94 | 98 | | 35 | | 27 |
| F | 0 | 133 | 133 | infinity | | infinity | |
| G | 74 | 72 | 102 | | 38 | | −3 |
| H | 199 | 217 | 300 | | 38 | | |
| J | 131 | 139 | 192 | | 47 | | 6 |
| | | | | Average | | Average | |
| Average RRs in categories | 106.6111 | 138.8889 | 175.4444 | | 37.375 | | 12.2857143 |

Please note the National mode for this rate of reading test is 100 wpm. Without intervention the Top quartile starts at 115 wpm. Less than 85 wpm is the bottom quartile. Greater than 115 is the top quartile.
University students normally have a reading rate of greater than 110 wpm. Examination results can be shown to closely follow these values rather than IQ.
The gains are NOT restricted to the poorest readers, but these get the highest gains interms of moving up the 'ranks' into functional literacy.

What is claimed is:

1. A method of testing applicable to the provision of a vision aid having colorimetric parameters, the method comprising the steps of:
   a. providing a vision aid having a chosen value of colorimetric parameters;
   b. assessing a visual benefit provided by said vision aid, said step of assessing the visual benefit provided by said vision aid comprising the steps of:
      i. carrying out an optical test in which said vision aid is used optically by said patient to identify a patient response to said test;
      ii. observing said patient response and deriving quantitative data representing said visual benefit to that particular patient; and
      iii. interpreting said quantitative data to identify a value of said colorimetric parameters of said vision aid which improves said benefit for said particular patient; and
   c. determining whether a different vision aid having a differing chosen value of said colorimetric parameters would produce a better result.

2. A method of testing applicable to the provision of a vision aid having colorimetric parameters, comprising the steps of:
   carrying out a test in which a vision aid having a value of colorimetric parameters is used by a patient to identify patient response to the test, and
   deriving quantitative data representing a visual benefit to the patient of said vision aid.

3. A method according to claim 1, wherein said step of observing said response to said test includes the step of determining a value which can be applied to the patient's response to a required task.

4. A method according to claim 3, wherein said value is recorded with respect to one of the following:
   all three values of hue, saturation and luminosity of the tested vision aid in three-dimensional perceived colour space, and
   all three values of red/green/blue elements of biological/physical colour space.

5. A method according to claim 1, wherein said optical test includes only one of the following steps:
   an array task, and
   a non-array task.

6. A method according to claim 3, wherein:
   said task comprises one of:
      a reading rate test, and
      other array task, and
   said value is a numerical value comprising one of the following:
      a number of words read per unit time, and
      other measure of said other array task.

7. A method according to claim 3, wherein said value is a numerical value comprising a count/analysis of eye movements of said patient during said test.

8. A method according to claim 6, further comprising the step of providing apparatus adapted to measure a quantitative value of said response of said patient to said test.

9. A method of testing applicable to the provision of a vision aid having colorimetric parameters, comprising the steps of
   carrying out at least two optical tests in which vision aids having different values of said colorimetric parameters are tested by a patient to identify patient response to the tests, with said tests being only one of the following:
      array tasks, and
      non-array tasks;
   deriving quantitative data representing a visual benefit to a patient of said vision aids; and
   interpreting said quantitative data to select a value of said colorimetric parameters of said vision aid which corresponds to an optimum visual benefit to the patient.

10. A method of testing applicable to the provision of a vision aid having colorimetric parameters, comprising the steps of:
    carrying out at least two optical tests in which vision aids having different values of said colorimetric parameters are tested by a patient,
    deriving from said tests quantitative data to provide values of said colorimetric parameters in color space, said values providing an at least approximate visual benefit to the patient, and
    interpreting said values to select a value of said colorimetric parameters of said vision aid which corresponds to an optimum visual benefit to the patient.

11. A method according to claim 3, wherein said value is a numerical value.

12. A method according to claim 2, wherein said test includes only one of the following steps:
an array task, and
a non-array task.

13. A method according to claim 7, further comprising the step of providing apparatus adapted to measure a quantitative value of said response of said patient to said test.

* * * * *